United States Patent [19]
Myers

[11] Patent Number: 5,624,447
[45] Date of Patent: Apr. 29, 1997

[54] SURGICAL TOOL GUIDE AND ENTRY HOLE POSITIONER

[75] Inventor: Reese K. Myers, Warsaw, Ind.

[73] Assignee: Othy, Inc., Warsaw, Ind.

[21] Appl. No.: 407,216

[22] Filed: Mar. 20, 1995

[51] Int. Cl.$^6$ ................................................. A61B 17/56
[52] U.S. Cl. ............................... 606/96; 606/86; 606/104
[58] Field of Search ................................. 606/86, 96, 97, 606/98, 103, 104, 191

[56] References Cited

U.S. PATENT DOCUMENTS

| | | | |
|---|---|---|---|
| 2,181,746 | 11/1939 | Siebrandt | 606/96 |
| 4,449,532 | 5/1984 | Storz | 606/191 |
| 4,549,538 | 10/1985 | Schadrack, III et al. | 606/96 |
| 4,821,716 | 4/1989 | Ohajar et al. | 606/96 |
| 4,927,424 | 5/1990 | McConnell et al. | 606/96 |
| 5,108,405 | 4/1992 | Mikhail et al. | 606/80 |
| 5,112,336 | 5/1992 | Krevolin et al. | 606/96 |
| 5,147,367 | 9/1992 | Ellis | 606/96 |
| 5,312,409 | 5/1994 | McLaughlin et al. | 606/96 |
| 5,409,493 | 4/1995 | Greenberg | 606/96 |

Primary Examiner—Michael Powell Buiz
Assistant Examiner—Mark S. Leonardo
Attorney, Agent, or Firm—Lundy and Associates

[57] ABSTRACT

In the broader aspects of the invention, there is provided an improved surgical tool guide and entry hole positioner comprising at least one cannulated sleeve with a handle and soft tissue protector secured to the sleeve. The cannulated sleeve has an inner surface which serves as a guide surface for a surgical tool and an obturator at one end thereof which fits in the cannulated sleeve. An improved method for locating the starting hole and accessing the intramedullary canal of bones such as the femur, the tibia, and the humerus is also provided including the steps of exposing the end of the intramedullary canal, positioning the tip of the sleeved guide with obturator in close proximity to the end of the canal, removing the obturator so that the cannulated sleeve remains in position, placing a guide pin through the sleeve and into the bone for radiographic evaluation of the guide pin placement, positioning a cannulated surgical tool over the guide pin, and using a cannulated drill for creating the entry hole into the bone for access to the intramedullary canal with a reamer, and introducing reamers and other surgical tools, guided by the inner surface of the sleeve into the intramedullary canal to increase the inner diameter of the canal until it is of a suitable diameter to receive a fracture fixation device, all the while retracting and protecting muscle, skin, and other soft tissue from damage.

17 Claims, 3 Drawing Sheets

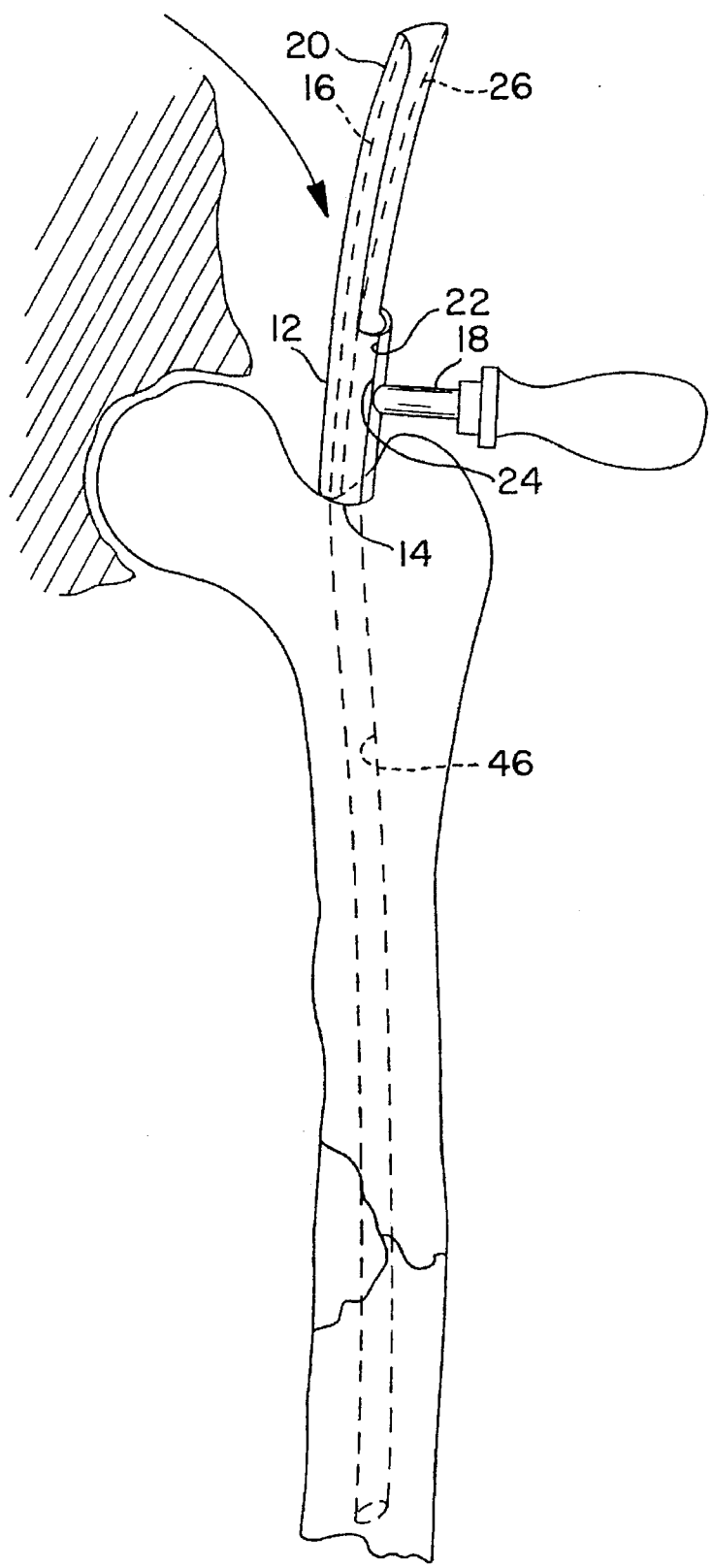
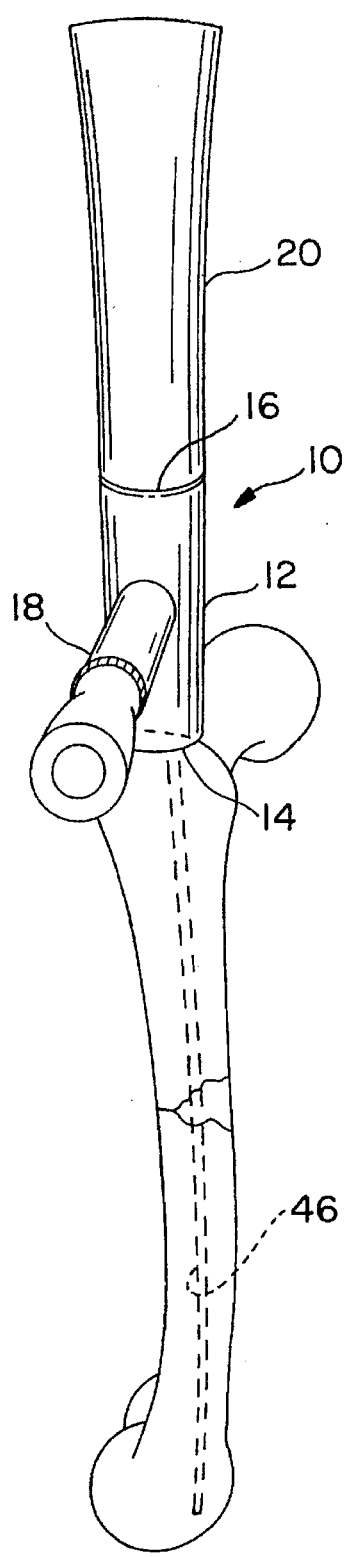
FIG. 1
FIG. 2

SURGICAL TOOL GUIDE AND ENTRY HOLE POSITIONER

The present invention relates to a surgical tool guide and entry hole positioner and a method for accessing the intramedullary canal of a bone, and more particularly to a surgical tool guide for reamers, drills, and the like for preparing the intramedullary canal of a bone to receive an intramedullary fracture reduction device.

Bone fractures have long been repaired by inserting fracture reduction rods into the intramedullary canal of the bone so as to span the fracture. In conducting this type of surgery for femoral fractures, it has been conventional to make an incision extending proximally from the flare of the greater trochanter so that the piriformis fossa may be palpated, and to access the intramedullary canal using an awl to form an entry hole at the piriformis fossa of the greater trochanter. While it has proven relatively easy to locate and palpate the piriformis fossa of the greater trochanter, it is more difficult to correctly position an entry hole to the intramedullary canal on the greater trochanter and to ream the canal to the desired size without damaging the surrounding soft tissue, displacing the previously reduced fracture, or making extremely large incisions, especially if the patient is obese or if flexion and abduction of the proximal fragment causes the tip of the greater trochanter to lie against the ilium. It is therefore highly desirable to provide an improved surgical tool guide and entry hole positioner and method for accessing the intramedullary canal of bones.

Recent surgical techniques have progressed to provide for intraoperation placement of instruments and implants utilizing radiographic visualization techniques. In utilizing these radiographic visualization techniques and conventional hole placement techniques, the surgeon and patient can be exposed to increased amounts of radiation. It is therefore highly desirable to provide an improved surgical tool guide and entry hole positioner and method of accessing the intramedullary canal utilizing these radiographic visualization techniques while minimizing the duration of the surgeon's and patient's radiographic exposure.

In utilizing radiographic visualization techniques, the incision is made only large enough to position the surgical tool on the bone. However, soft tissue damage may result from the tool because of the small incision and the proximity of the tool to the tissue. Therefore it is highly desirable to provide an improved surgical tool guide and entry hole positioner which has a protective shield by which soft tissue may be kept from the tool and soft tissue injury may be minimized.

Traditional methods for creating the entry hole into the bone employ an awl to manually perforate the hard cortical bone with oscillatory motions which displace and can further fragment the fracture. Therefore, it is highly desirable to provide an improved surgical tool guide and entry hole positioner which allows for the creation of an entry hole into a bone while minimizing any resultant displacement or fragmentation of the fracture.

In placing a fracture fixation rod in the intramedullary canal of a bone, it is essential that an entry opening be properly positioned and the canal be reamed to a size to receive a rod of a suitable size so that the ensuing fracture reduction is suitably aligned. Thus it is necessary for an entry hole to be properly positioned and a series of reamers to be utilized to ream the canal to the appropriate size. Therefore, it is highly desirable to provide an improved surgical tool guide and entry hole positioner which allows for the surgeon to accurately position the entry hole and to guide reamers into the intramedullary canal of the bone and to ensure the desired reduction of the fracture.

Iatrogenic fracture of the bone can occur when the axis of the reamed portion of the intramedullary canal does not align with the anatomic longitudinal axis of the bone. It is therefore highly desirable to provide an improved surgical tool guide and entry hole positioner by which both rigid and flexible reamers can be utilized and properly guided into the intramedullary canal and the canal may be prepared with a contour better corresponding to the anatomic longitudinal axis of the bone.

Many well documented risks are associated with anesthesia and the risks to the patient increase with the duration of the applied anesthesia. It is therefore highly desirable to provide an improved surgical tool guide and entry hole positioner and method of accessing the intramedullary canal which would minimize operative time and decrease the patient's exposure to anesthesia.

Surgical infection rates are known to increase substantially with the length of operative time necessary to complete a given procedure. It is therefore highly desirable to provide an improved surgical tool guide and entry hole positioner which would minimize operative time, thereby decreasing the patient's risk of infection.

Finally, it is highly desirable to provide an improved surgical tool guide and entry hole positioner and method of accessing the intramedullary canal of a bone which possesses all of the above-identified features.

SUMMARY OF THE INVENTION

It is therefore an object of this invention to provide an improved surgical tool guide and entry hole positioner and method of accessing the intramedullary canal of bones.

It is also an object of the invention to provide an improved surgical tool guide and entry hole positioner and method for accessing the intramedullary canal of a bone which benefits the patient and surgeon by minimizing radiographic exposure.

It also an object of the invention to provide an improved surgical tool guide and entry hole positioner which has a protective shield by which soft tissue may be kept from the tool and soft tissue injury may be minimized.

It is also an object of the invention to provide an improved surgical tool guide and entry hole positioner and method for accessing the intramedullary canal of a bone which allows for the creation of an entry hole into a bone while minimizing any resultant displacement or fragmentation of the fracture.

It is also an object of the invention to provide an improved surgical tool guide and entry hole positioner which allows for the surgeon to accurately position the entry hole and to guide reamers into the intramedullary canal of the bone and reaming the canal to the appropriate size to ensure that a fracture fixation device, when implanted in the reamed canal, may be properly aligned with respect to the anatomy.

It is also an object of the invention to provide an improved surgical tool guide and entry hole positioner which allows for the surgeon to accurately position the entry hole to minimize the possibility of iatrogenic fracture of the proximal fracture fragment due to mal-positioning of the entry hole.

It is also an object of the invention to provide an improved surgical tool guide and entry hole positioner which allows for the surgeon to accurately position the entry hole which would minimize the amount of operative time necessary to locate and create the entry hole and to ream the intramedullary canal, minimizing the duration of the patient's anesthesia and its subsequent risks.

It is also an object of the invention to provide an improved surgical tool guide and entry hole positioner which allows for the surgeon to accurately position the entry hole which would minimize the amount of operative time necessary to locate and create the entry hole and to ream the intramedullary canal, minimizing the patient's risk of infection.

It is also an object of the invention to provide an improved surgical tool guide and entry hole positioner by which both rigid and flexible reamers can be utilized and properly guided into the intramedullary canal of a bone so that the canal has a contour and longitudinal axis which corresponds to the anatomic longitudinal axis of the bone.

It it finally an object of the invention to provide an improved surgical tool guide and entry hole positioner and method of accessing the intramedullary canal of a bone which possesses all of the above-identified features.

In the broader aspects of the invention, there is provided an improved surgical tool guide and entry hole positioner comprising at least one cannulated sleeve with a handle and soft tissue protector secured to the sleeve. The cannulated sleeve has an inner surface which serves as a guide surface for a surgical tool and an obturator at one end thereof which fits in the cannulated sleeve.

An improved method for locating the starting hole and accessing the intramedullary canal of bones such as the femur, the tibia, and the humerus is also provided including the steps of exposing the end of the intramedullary canal, positioning the tip of the sleeved guide with obturator in close proximity to the end of the canal, removing the obturator so that the cannulated sleeve remains in position, placing a guide pin through the sleeve and into the bone for radiographic evaluation of the guide pin placement, postioning a cannulated surgical tool over the guide pin, and using a cannulated drill for creating the entry hole into the bone for access to the intramedullary canal with a reamer, and introducing reamers and other surgical tools, guided by the inner surface of the sleeve into the intramedullary canal to increase the inner diameter of the canal until it is of a suitable diameter to receive a fracture fixation device, all the while retracting and protecting muscle, skin, and other soft tissue from damage.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is a fragmentary diagrammatic view of a femur with the improved surgical tool guide in a flexible reamer and entry hole positioner having a curved axis positioned thereon and aligned with the intramedullary canal;

FIG. 2 is a view like FIG. 1 taken essentially in a direction 90 degrees from the direction of FIG. 1 showing the straight version of the improved surgical tool guide of the invention for a flexible reamer;

DESCRIPTION OF A SPECIFIC EMBODIMENT

Figure 3:
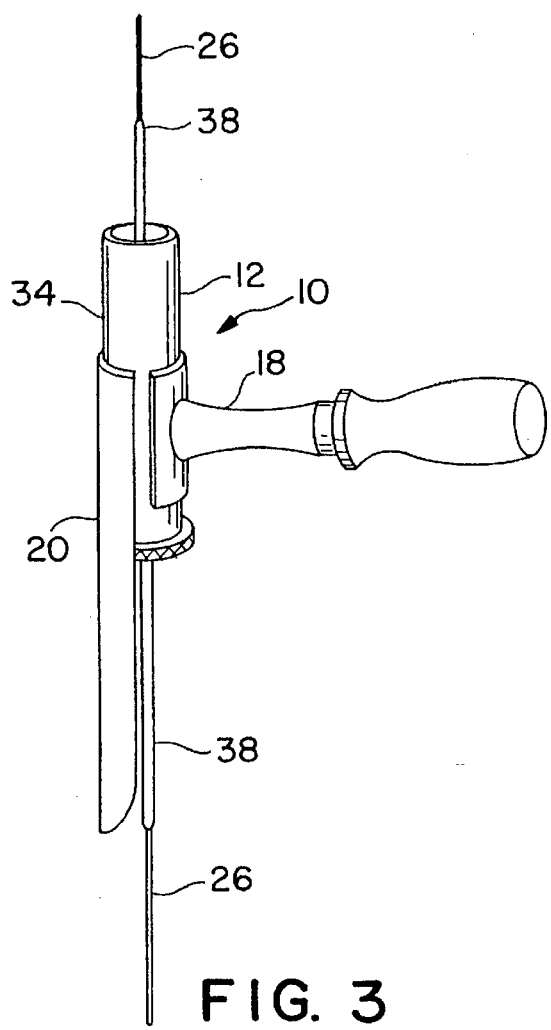
FIG. 3 is a perspective view of the straight version of the improved surgical tool guide of the invention with a guide pin extending therethrough and the handle and tissue shield connected thereto by a clamp.
Figure 4:
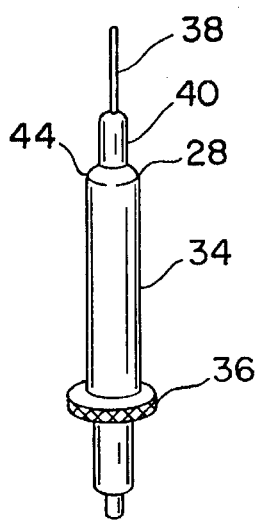
FIG. 4 is a perspective view of one of the cannula the improved surgical tool guide of the invention shown in FIG. 3 showing and a side cutting reamer positioned within the cannula and obturator of the tool guide on the guide pin.

The improved surgical tool guide and entry hole positioner 10 of the invention is shown in the Figures to include a sleeve or cannula 12 having opposite ends 14, 16. A handle 18 is secured to the sleeve 12. Handle 18 extends from sleeve 12 generally perpendicularly thereof and is secured to sleeve 12 between opposites ends 14, 16. Also secured to sleeve 12 is a protective tissue shield 20. Shield 20 extends generally axially of sleeve 12. Tissue shield 20 is secured to sleeve 12 at a position generally diametrically opposite of handle 18. In a specific embodiment, sleeve 12 is generally cylindrical and tissue shield 20 is also generally cylindrical. In a specific embodiment that has proven useful, protective tissue shield 20 has a radius of more than twice the radius of sleeve 12.

Sleeve 12 has an interior passage way 22 extending therethrough from end 14 to end 16. In a specific embodiment, sleeve 12 and passage way 22 are both flared adjacent end 16 to facilitate the positioning of a surgical tool therein even though the tool is not coaxially aligned with the sleeve 12. Passage way 22 has generally cylindrical interior surgical tool guiding surface 24 which proves useful to guide surgical tools such as flexible reamers as will be described hereinafter.

Figure 6:
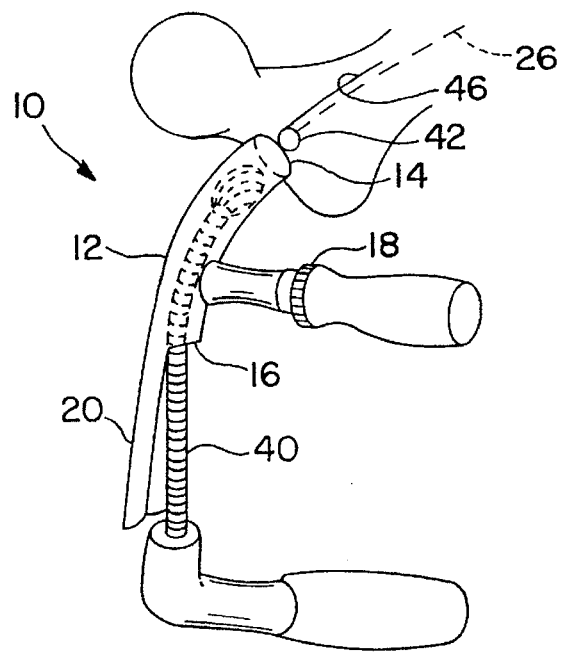
FIG. 6 is a view like FIG. 1 showing the curved version of the improved surgical tool guide of the invention with a flexible reamer positioned therein.

In each embodiment of the invent ion, sleeve 12 bas a longitudinal axis 26. In some embodiments of the surgical tool guide and entry hole positioner 10 of the invention axis 26 is straight as shown in FIGS. 2–4 and 1–4 In other specific embodiments, longitudinal axis 26 is curved as shown in FIGS. 1 and 6.

Telescopically positioned within sleeve 12 is a cannulated sleeve or cannula 28. Cannulated sleeve 28 has an interior passage 30 extending therethrough. Passage 30 has interior surgical tool guiding surfaces 32. Passage 30 of cannulated sleeve 28 may in some specific embodiments be the same size as passage 22 of sleeve 12; in other specific embodiments, passage 30 may be significantly smaller than passage 22 of sleeve 12. In some specific embodiments, passage 30 is generally cylindrical. The size of passages 22, 30 will be mentioned hereinafter depends upon the size of the surgical tool being used with the surgical tool guide and entry hole positioner of the invention.

In one version of the surgical tool guide and entry hole positioner 10 there is provided a plurality of sleeves 34. Each sleeve 34 has opposite ends 14 and 16 and a passage 22 extending therethrough. Each sleeve 34 has surgical tool guiding surfaces therein, a longitudinal axis 26 and a frustoconical portion 44 adjacent end 14 thereof. Each of the plurality of sleeves 34 are generally cylindrical and have a diametrical size such that they will nest within sleeve 12 in a telescoping fashion one within thin the other.

Each of the cannulated sleeves 34 have a passage 30 having a diametrical size proportional to the diameter of the cannulated sleeve 34.

Figure 5:
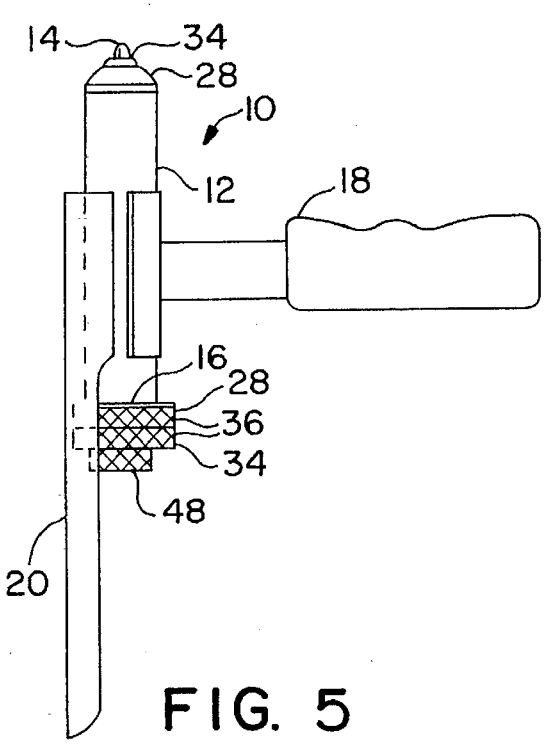
FIG. 5 is a perspective view of the improved surgical tool guide of the invention shown in FIG. 2 showing another manner by which the handle and tissue shield is attached, and which the obturator, and cannula are telescoped one within the other.
Figure 7:
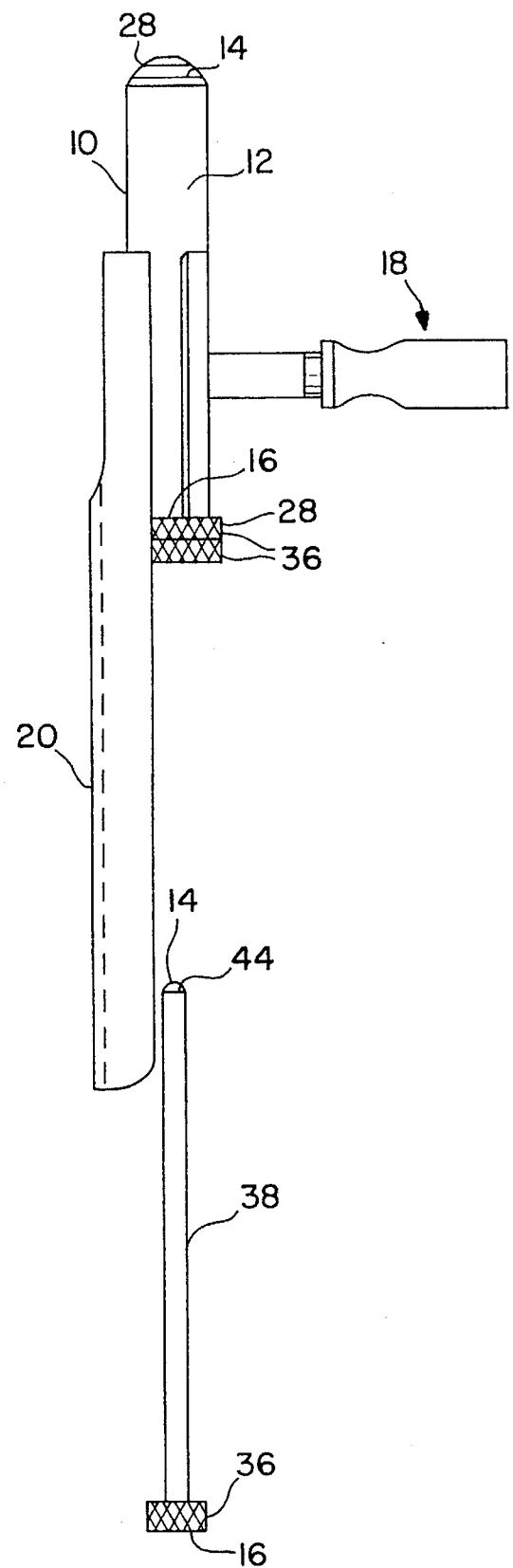
FIG. 7 is a view like FIG. 5 with the obturator thereof exploded therefrom.
Figure 8:
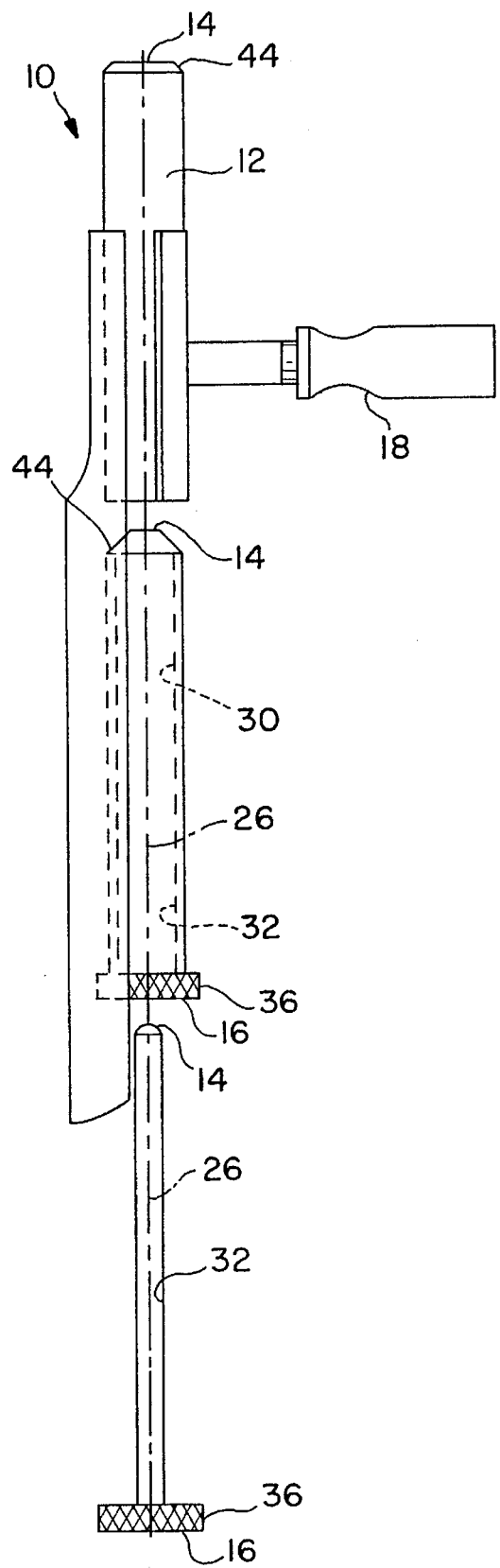
FIG. 8 is a view like FIGS. 5 and 7 with the two cannulae exploded therefrom.

In the specific embodiment illustrated in FIGS. 5, 7 and 8, the plurality of sleeves 34 and sleeve 28 are nested together as shown in FIG. 5.

In a specific embodiment, the handle 18 and soft tissue shield 20 are secured to opposite sides of a "C" clamp which can be positioned around sleeve 12 with the diametrical size of the "C" clamp and sleeve 12 chosen such that the "C" clamp is resiliently expanded so as to secure the handle and the soft tissue sleeve to the plurality of sleeves as shown in FIG. 3.

In the specific embodiments illustrated in FIGS. 3–5 and 7–8, each of the plurality of sleeves 34 have a longitudinal axis 26 which is straight and coincident and the sleeves 34 are nested, telescopically, one within the other.

In other specific embodiments, each of the telescoping plurality of sleeves 34 have adjacent ends 16 a flange 36 which extends generally perpendicularly from the sleeve 34. Flanges 36 are generally of the same size such that they stack one on top of the other when the sleeves are telescopically nested.

Each of the guiding surfaces 24, 32 of passages 22, 30 of sleeves 12 and 34 correspond to a surgical tool 40 used with the sleeve in a guiding relationship. These surgical tools 40 may be chosen from the group consisting of drills, reamers, Steinman pins, broaches and the like. The drills, reamers, broaches and Steinman pins and other surgical tools 40 may either be straight and rigid or flexible and may be either guided soley by the surgical guide surfaces 24 and 32 of the passages 22 and 30 or cannulated so as to be guided not only by the guide surfaces 24, 32 but also by a Steinman pin or guide pin 38 extending through the tool 40.

As in the performance of the method which will be described following hereinafter the size of the guide pin 38 may be changed from one of relatively small diameter to larger diameter Steinman or guide pins 38 as the performance of the method progresses. When this occurs, it may be necessary to remove one of the cannulated sleeves so as to guide a particular surgical tool.

In the specific embodiment illustrated, an obturator 48 is provided for positioning within the smallest sleeve 34. Obturator 48 has ends 14, 16 and a solid lip 36 at end 16 obturator 48 is solid and not cannulated. Positioned within the smallest sleeve 34, as shown in FIG. 5, the improved surgical tool guide 10 of the invention has each of the passages 22, and 30 filled and is not cannulated.

In operation, an improved surgical tool guide and entry hole positioner 10 is provided for use in positioning tools 40 within the intramedullary canal of a bone, typically, the femur, the tibia, or the humerus. The tool guide and entry hole positioner 10 also allows a surgeon to enter the intramedullary canal for any procedure where removal of bone marrow is desired.

Entering the intramedullary canal especially with a surgical tool for boring the canal and/or reaming the canal to the size of a fracture reduction rod is always difficult. Soft tissue surrounds the end of the canal and while the end of the canal can be exposed by incising the tissue, locating an appropriate hole to provide entry into the intramedullary canal has always posed significant problems. By the surgical tool guide and entry hole positioner 10 of the invention the surgeon may make an incision just large enough to receive the tool guide and position the tool guide end 14 with respect to the end of the canal of a bone by radiographic visualization techniques such that an entry hole can be properly made into the intramedullary canal by a drill positioned in the tool guide 10 and guided by the surfaces 24 and 32. The shield 20 of the surgical tool guide and entry hole positioner 10 of the invention holds the soft tissue away from the drill so as to minimize soft tissue damage during this procedure.

Once the entry hole is made, the intramedullary canal may be drilled, bone marrow removed or broached or reamed to size for an implant utilizing the surgical tool guide and entry hole positioner 10 in accordance with two related techniques of the method of the invention. The intramedullary canal can be drilled and reamed to the desired size utilizing the surgical tool guide and entry hole positioner 10 of the invention after the entry hole has been made by utilizing the surgical tool guide 10 having a plurality of sleeves 34 telescopically nesting one within the other.

First utilizing all of the sleeves 34 initially, a drill is extended into the intramedullary canal to form an entry hole 42 and a bore 46 therein. The drill is guided by the guiding surfaces 24 of the smallest interior sleeve of the plurality of sleeves 34 and by the guiding surface 32 thereof.

The bore 44 is then enlarged by passing a cannulated reamer of a slightly larger diameter than bore 42 over the guide pin 48 and into the bore 42. A side cutting reamer with a blunt tip may be utilized for this purpose. The smallest sleeve is removed from the telescopically nested sleeves 34 to expose a larger sleeve for guiding the reamer into the entry hole and into the bore 42 within the intramedullary canal. Again, guiding surfaces 32 of the passage 30 of the sleeve 34 guides the reamer as desired.

In a specific embodiment, a Steinman or guide pin 38 is driven into the bore 42 and the drill and reamer utilized is cannulated so as to receive the Steinman or guide pin within an interior bore in the drill and/or reamer extending from end to end. In this specific embodiment, the drill and reamer is guided both by the exterior surface of the guide pin and the interior guiding surfaces 24 and 32 of the passage 22 of the sleeve 34 and the obturator 28, respectively.

The bore 10 is further enlarged by removing the interior next smallest sleeve 34 of the telescoping sleeves 34 and inserting still a larger side cutting reamer within the sleeve 34 and within the bore 42 guided by the interior surfaces 24 of the passage 22 of the sleeve 34 and the interior guiding surfaces 32 of the passage 30. This step is repeated until the bore within the intramedullary canal has sufficient size to receive a fracture fixation rod.

Alternatively, a curved surgical tool guide and entry hole positioner 10 of the invention is utilized. Curved surgical tool guide and entry hole positioner includes a sleeve 12 which has a longitudinal axis 26 which is curved rather than straight and a passage 22 extending from end to end with interior tool guiding surfaces 24 therein. Flexible reamers can be used with this guide in a manner similar to the use of the tool guide 10 having telescopically nested sleeves 34 therein above-described. However, because of the construction of the flexible tools utilized with the tool guide 10 of the invention once the entry hole is made by a drill, the reamers can be utilized with the tool guide in the same manner, as above-described without exchanging sleeves as the reamer size increases. The passages 22, 30 and the guiding surfaces 24, 32 are slightly larger than the largest tool to be used, and of the surgical tool guide 10 remains the same throughout the entire procedure. The tips of the flexible reamer are merely enlarged incrementally so as to ream the intramedullary canal to a size large enough to receive the fracture fixation rod.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A surgical tool guide and entry hole positioner comprising an outer sleeve having a distal end and a proximal end and a longitudinal axis, a soft tissue shield extending proximally and axially from the proximal end of said outer sleeve, a handle secured to said outer sleeve, said outer sleeve having an interior passage extending therethrough and interior guide surfaces for insertion of a surgical tool, the size of said surgical tool being limited by the diameter of said interior passage of said outer sleeve, said surgical tool being inserted into the proximal end of said outer sleeve with the distal end of said outer sleeve being directed toward an intramedullary canal of a bone so as to accurately form an entry hole from an external surface of the bone to the intramedullary canal of the bone coaxial with the longitudinal anatomical axis of said bone, a plurality of removably nested sleeves, each of said nested sleeves having a distal end and an enlarged proximal end, each of said nested sleeves having an interior passage, each of which nested sleeves may also guide a surgical tool so as to accurately form an entry hole from the external surface of a bone to an intramedullary canal of said bone coaxial with the longitudinal anatomical axis of said bone.

2. The surgical tool guide of claim 1 wherein said sleeve has a longitudinally extending axis.

3. The surgical tool guide and entry hole positioner of claim 1 wherein said outer sleeve and said nested sleeves are generally tubular.

4. The surgical tool guide and entry hole positioner of claim 1 wherein said handle extends from said outer sleeve generally perpendicular to the longitudinal axis of said outer sleeve.

5. The surgical tool guide and entry hold positioner of claim 1 wherein said tissue shield has a proximal end and a distal end, said distal end of said tissue shield being attached to said proximal end of semi-tubular extension of said outer sleeve.

6. The surgical tool guide and entry hole positioner of claim 1 wherein said tissue shield has a radiused curvature such that said radius increases from said distal end to said proximal end, said radius of said distal end being larger than the outer diameter of the nested sleeve of greatest outer diameter.

7. The surgical tool guide and entry hole positioner of claim 1 wherein said largest of said nested sleeves is secured in said outer sleeve by a clamping mechanism extending through the longitudinal axis of said handle, said clamping mechanism being removably positioned on said nested sleeve of largest diameter.

8. The surgical tool guide and entry hold positioner of claim 1 further comprising a plurality of said nested sleeves, each of said sleeves having an enlarged proximal end and a distal end which is generally frusto conical in shape, with the largest of said nested sleeves having an inner passage of diameter greater than the outer diameter of a second sleeve, with said second sleeve being greater in length than the said largest sleeve such that when nested completely in said largest sleeve their distal ends are coplanar, with said second sleeve having an inner passage of diameter greater than the outer diameter of a third sleeve, with said third sleeve being greater in length than said second sleeve such that when nested completely in said second sleeve their distal ends are coplanar, with said third sleeve having an interior passage.

9. The surgical tool guide of claim 1 wherein said surgical tools are cannulated.

10. The surgical tool guide of claim 1 wherein said nested sleeves have coincident curved axes.

11. The surgical tool guide of claim 8 wherein there are tow sleeves of said plurality.

12. The surgical tool guide and entry hole positioner of claim 8 further comprising an obturator with an enlarged proximal end and a distal end, said obturator having a conical distal end coming to a sharp point, said obturator having a diameter smaller than the diameter of the interior passage of said second sleeve, said obturator being greater in length than said second sleeve such that when nested completely in said second sleeve said conical portion of said obturator protrudes beyond the distal end of said second sleeve.

13. The surgical tool guide of claim 8 further comprising surgical tools for use with said nested sleeves, one such tool being a reaming tool with a proximal end and a distal end, said reaming tool being longer than said third sleeve, said reaming tool having an interior passage of the same diameter as the interior passage of said third sleeve, said reaming tool having an outer diameter less than the diameter of said interior passage of said second sleeve.

14. The surgical tool guide of claim 8 further comprising surgical tools for use with said nested sleeves, one such tool being a pin with a proximal end and a distal end having a sharp cutting tip, said pin being longer than said third sleeve, said pin having a diameter less than the diameter of the interior passage of said reaming tool.

15. The surgical tool guide of claim 8 wherein each of said nested sleeves have an enlarged proximal end, said ends being stacked when said sleeves are nested.

16. The surgical tool guide of claim 8 wherein each of said nested sleeves has a longitudinal axis, said axes being coincident when said sleeves are nested.

17. The surgical tool guide of claim 15 wherein said surgical tools are chosen from the group consisting of reamers, broaches and drills.

* * * * *